United States Patent
Mokelke et al.

(10) Patent No.: US 8,849,395 B2
(45) Date of Patent: Sep. 30, 2014

(54) GUIDE CATHETER HAVING VASOMODULATING ELECTRODES

(75) Inventors: Eric A. Mokelke, White Bear Lake, MN (US); Robert Shipley, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1292 days.

(21) Appl. No.: 12/130,809

(22) Filed: May 30, 2008

(65) Prior Publication Data
US 2009/0299443 A1 Dec. 3, 2009

(51) Int. Cl.
- *A61N 1/00* (2006.01)
- *A61N 1/05* (2006.01)
- *A61N 1/36* (2006.01)

(52) U.S. Cl.
CPC .............. *A61N 1/05* (2013.01); *A61N 1/36014* (2013.01); *A61N 1/36117* (2013.01)
USPC ............................................................ 607/2

(58) Field of Classification Search
USPC .......................................... 607/2, 44, 72, 74
See application file for complete search history.

(56) References Cited

U.S. PATENT DOCUMENTS

| | | |
|---|---|---|
| 373,339 A | 11/1887 | Clifford |
| 3,301,258 A | 1/1967 | Werner et al. |
| 4,016,886 A | 4/1977 | Doss et al. |
| 4,043,338 A | 8/1977 | Homm et al. |
| 4,119,102 A | 10/1978 | LeVeen |
| 4,154,246 A | 5/1979 | LeVeen |
| 4,312,364 A | 1/1982 | Convert et al. |
| 5,135,478 A | 8/1992 | Sibalis |
| 5,188,602 A | 2/1993 | Nichols |
| 5,304,120 A | 4/1994 | Crandell et al. |
| 5,437,664 A | 8/1995 | Cohen et al. |
| 5,458,596 A | 10/1995 | Lax et al. |
| 5,498,238 A | 3/1996 | Shapland et al. |
| 5,501,662 A | 3/1996 | Hofmann |
| 5,507,724 A | 4/1996 | Hofmann et al. |
| 5,554,119 A | 9/1996 | Harrison et al. |
| 5,626,576 A | 5/1997 | Janssen |

(Continued)

FOREIGN PATENT DOCUMENTS

| | | |
|---|---|---|
| GB | 2 333 964 | 8/1999 |
| WO | 98/55072 | 12/1998 |

OTHER PUBLICATIONS

Buga, Georgette M. et al. "Electrical Field Stimulation Causes Endothelim-Dependent and Nitric Oxide-Mediated Relaxation of Pulmonary Artery," Am J Physiol Heart Circ Physiol 262: H973-H979, 1992.

(Continued)

*Primary Examiner* — Scott Getzow
(74) *Attorney, Agent, or Firm* — Seager, Tufte & Wickhem, LLC

(57) ABSTRACT

A guide catheter system includes a guide catheter having a proximal end, a distal end, an outer wall and a first, second and third electrode wherein the first, second and third electrodes are spaced longitudinally apart from each other on the outer wall of the catheter, and an electrical impulse generator connected to the guide catheter wherein the electrical impulse generator includes a circuit for selecting an adjacent pair of electrodes to use as a bipolar electrode system to send an electrical impulse and a method of use thereof to treat vasospasm.

14 Claims, 4 Drawing Sheets

(56) References Cited

U.S. PATENT DOCUMENTS

| | | | |
|---|---|---|---|
| 5,634,899 | A | 6/1997 | Shapland et al. |
| 5,643,257 | A | 7/1997 | Cohen et al. |
| 5,690,691 | A | 11/1997 | Chen et al. |
| 5,704,908 | A | 1/1998 | Hofmann et al. |
| 5,709,224 | A | 1/1998 | Behl et al. |
| 5,810,804 | A | 9/1998 | Gough et al. |
| 5,817,092 | A | 10/1998 | Behl |
| 5,827,268 | A | 10/1998 | Laufer |
| 5,863,290 | A | 1/1999 | Gough et al. |
| 5,868,740 | A | 2/1999 | LeVeen et al. |
| 5,944,710 | A | 8/1999 | Dev et al. |
| 6,014,584 | A | 1/2000 | Hofmann et al. |
| 6,014,589 | A | 1/2000 | Farley et al. |
| 6,026,326 | A | 2/2000 | Bardy |
| 6,036,687 | A | 3/2000 | Laufer et al. |
| 6,132,419 | A | 10/2000 | Hofmann |
| 6,149,681 | A | 11/2000 | Houser et al. |
| 6,152,899 | A | 11/2000 | Farley et al. |
| 6,219,577 | B1 | 4/2001 | Brown, III et al. |
| 6,258,084 | B1 | 7/2001 | Goldman et al. |
| 6,845,267 | B2 | 1/2005 | Harrison et al. |
| 6,865,416 | B2 * | 3/2005 | Dev et al. ............................ 607/2 |
| 6,939,345 | B2 | 9/2005 | KenKnight et al. |
| 6,973,352 | B1 * | 12/2005 | Tsutsui et al. ................. 607/122 |
| 2004/0162584 | A1 * | 8/2004 | Hill et al. ............................ 607/3 |
| 2007/0191904 | A1 | 8/2007 | Libbus et al. |
| 2007/0260281 | A1 | 11/2007 | Hastings et al. |
| 2008/0188913 | A1 | 8/2008 | Stone et al. |
| 2008/0195174 | A1 * | 8/2008 | Walker et al. ................... 607/44 |

OTHER PUBLICATIONS

Cragg, Andrew H, M.D. et al., "Endovascular Diathermic Vessel Occlusion," Radiology vol. 144, No. 2, pp. 303-308, Jul. 1982.

Duckles, Sue Piper et al., "Transmural Nerve Stimulation of Blood Vessels in vitro: a Critical Examination," Blood Vessels 17:53-57 (1980).

Feletou, M. et al., "Relaxation of Canine Coronary Artery to Electrical Stimulation: Limited Role of Free Radicals," Am J Physiol Heart Circ Physiol 253: H884-H889, 1987.

Frank, Gerard W. et al., "Electrical Stimulation Causes Endothelium-Dependent Relaxation in Lung Vessels," Am J Physiol Heart Circ Physiol 244:793-798, 1983.

Geary, G.G. et al., "Endothelium-Dependent Vascular Smooth Muscle Relaxation Activated by Electrical Field Stimulation," Acta Physiol Scand. 1997; 160:219-228.

Gustafsson, Finn et al., "Conducted Vasoconstriction in Rat Mesenteric Arterioles: Role for Dihydropyridine-Insensitive Ca2+ Channels," Am J Physiol Heart Circ Physiol 280:H582-H590, 2001.

Lamb, Fred S. et al., "Vascular Effects of Free Radicals Generated by Electrical Stimulation," Am J Physiol Heart Circ Physiol 247:H709-H714, 1984.

Marin, J. et al., "Vasoconstriction of the Isolated Communicating Cerebral Artery Induced by Field Electrical Stimulation," Rev Esp Fisiol. Sep. 1979;35(3):353-8 (abstract).

O'Reilly, Kevin, "A Technique of Diathermy Sclerosis of Varicose Veins," Aust. N.Z. J. Surg. vol. 51. No. 4, Aug. 1981, pp. 379-382.

O'Reilly, Kevin, "Endovenous Diathermy Sclerosis as a Unit of the Armamentarium for the Attack on Varicose Veins," The Medical Journal of Australia, vol. 1—61st Year, No. 22, Jun. 1, 1974, p. 900.

O'Reilly, Kevin, "Endovenous Diathermy Sclerosis of Varicose Veins," Aust. N.Z. J. Surg. vol. 47. No. 3, Jun. 1977, pp. 393-395.

Partsch, Hugo M.D., "Compression Therapy of the Legs," J Dermatol Surg Oncol 1991; 17:799-805.

Sarin, S. et al., "Mechanism of Action of External Compression on Venous Function," Br. J. Surg. vol. 79, No. 6, Jun. 1992, pp. 499-502.

van Bemmelen, Paul S. M.D., et al., "Quantitative Segmental Evaluation of Venous Valvular Reflux with Duplex Ultrasound Scanning," J. Vasc. Surg., vol. 10, No. 4, Oct. 1989, pp. 425-431.

Watts, G.T., "Endovenous Diathermy Destruction of Internal Saphenous," Br. Med. J., vol. 4, Oct. 7, 1972, p. 53 (abstract).

Zhang, Wei et al., "Sympathetic Cotransmission in Rabbit Saphenous Artery in vitro: Effect of Electric Stimulation and Potentiation by α, β-methylene ATP," Acta Pharmocol Sin Oct. 2001; 22(10):907-912.

* cited by examiner

GUIDE CATHETER HAVING VASOMODULATING ELECTRODES

FIELD

This invention relates to the field of vessel vasomodulation, vasodilation and vasoconstriction using electrical impulses and guide catheters that have such a vasomodulating function and methods of use thereof.

BACKGROUND

During catheterization procedures, the introduction of guidewires, guide catheters or other instruments may stimulate an unwanted vasospasm, which creates narrowing of the blood vessel. Typical treatments are to wait for the vasospasm to relax, add a vasorelaxant such as nitroglycerine, or risk damage to the narrowed lumen of the vessel by continuing the procedure. Waiting for the spasm to resolve increases procedure time, and adding nitroglycerine may cause unwanted systemic effects of reducing blood pressure. There is thus a need to provide a means to treat vasospasms in an acute setting in a manner that is preferably immediate and local.

SUMMARY

One embodiment of the invention, therefore, pertains to a catheter that can provide immediate, local electrical stimulation to treat vasospasms. Electrical stimulation can cause both vasodilation and vasoconstriction. The stimulating waveform completely determines whether the vessel will constrict or dilate. Frequency, voltage and duration of the stimulating pulse can be selected to dilate a vessel that experiences local spasms and constriction. A catheter having a unipolar or, alternatively, a bipolar electrode at the distal tip or at a distal location along the catheter outer surface along with a controller attached at the catheter proximal end for determining and generating the waveform signal can be used for catheterization procedures. If the vessel undergoing intervention begins to spasm and constrict, the stimulation can be turned on to cause vasorelaxation and the procedure can be continued with minimal interruption. This can be repeated as often as necessary throughout the procedure.

Another embodiment pertains to a guide catheter that includes an electrode on its distal tip. Such an electrode may be a bipolar electrode having two exposed conducting elements at the distal tip of the guide catheter that are electrically connected to a signal generation device electrically connected to the electrode through the base of the guide catheter. An alternate construction is a monopolar electrode configuration with a single conducting element at the distal tip of the guide catheter and a return electrode disposed at the proximal base of the catheter or at some other suitable location. An additional alternative embodiment includes a guide catheter configuration that has a single electrode at its distal end and also includes a conducting guidewire that can act as a return electrode and is disposed through the lumen of the guide catheter during operation.

One method of use involves using the system to treat vasospasms that may occur as the guide catheter is advanced distally through the vasculature. A vasospasm is a spasm of the blood vessel and may lead to constriction of the vessel. Vasospasms may be caused by irritation of the blood vessel lining, irritation caused by the condition being treated, medical devices being advanced through the blood vessel, therapeutic procedures or some other cause. The blood vessel is monitored as the guide catheter is advanced, either fluoroscopically, through one of the known rapid scanning techniques or through another suitable method. When a vasospasm or other constriction is encountered, the electrode is activated as described in more detail below to provide relief to the vasospasm. Such relief can include restoring the blood vessel to its normal diameter or may include causing the blood vessel to temporarily expand to larger than its normal diameter. The guide catheter may then be advanced while being monitored and the procedure repeated as desired.

Another method of use involves using the tip electrode guide catheter embodiment to help advance the distal tip of the catheter from a larger vessel into a smaller vessel branching from the larger vessel or at a bifurcation in a vessel. Generally the guide catheter is advanced, preferably along a guidewire, to a position in the larger vessel close to where the lumen of the smaller vessel opens in the wall of the larger vessel. The tip electrode is activated as described in more detail below to dilate the opening, and the distal tip of the guide catheter is advanced into the lumen of the smaller vessel. Such a procedure may be of use in any number of places in the vasculature, including in the heart and in other organs and may also be of use in any of the other body vessels having a similar configuration. For example, the procedure may be of use in an endoscopic procedure to dilate or calm the papilla of Vater prior to advancing a catheter or other therapeutic instrument through the opening.

Another method of use involves advancing the tip electrode guidewire through a vessel to an occlusion such as a fatty deposit on the wall of the blood vessel. When the tip electrode is near the occlusion, the electrode is activated to relax and possibly dilate the wall of the blood vessel prior to advancing a guidewire or other therapeutic instrument such as an angioplasty catheter through the occlusion. The stimulation from the electrode may also be continued while the therapeutic device is being advanced.

Another embodiment pertains to an indifferent electrode guide catheter system where the guide catheter includes along a portion of its length a conducting material that serves as one half (anodic or cathodic) of a bipolar electrode. The conducting material is electrically connected to a pin at the proximal base or hub of the guide catheter. The system also includes a return electrode on a separate device such as a guidewire that has an exposed conducting portion at its distal end electrically connected to a pin at its proximal end. The system includes an electrical signal generator that can be electrically connected to the guide catheter and return electrode as desired.

In a method of use, the indifferent electrode guide catheter may be used as an ordinary guide catheter until a vasospasm or other incidence is encountered. For example, the indifferent electrode guide catheter may be advanced along a guidewire to a position in the aorta. If vasomodulation is desired, the return electrode may be advanced along a parallel vessel, which in this example may be the vena cava, until the distal end of the return electrode is located at the desired location for vasomodulation. The electrical signal generator is connected to the guide catheter and the return electrode, and a signal is generated to vasomodulate the vessel. The vasomodulation occurs around the portion of the conduction material on the guide catheter that is nearest to the distal tip of the return electrode. The return electrode may be moved as desired to vasomodulate different areas of the vessel.

Another embodiment pertains to a guide catheter having a bipolar electrode at one or more areas along its length. Separate electrodes are disposed along the length of the outer surface of a guide catheter, and each electrode is separately electrically connected to a separate pin at the base of the guide catheter. Each electrode is a patch of electrically conducting material at the surface of the catheter, and each electrode may extend circumferentially around the guide catheter. An alternative embodiment includes a tip electrode such as described above with respect to the tip electrode guide catheter embodiment. A signal generating device may be connected to the pins at the base of the guide catheter. The operator can use the signal generating device to select any consecutive pair of electrodes to send a vasomodulating signal to. Alternatively, the signal generating device can send a cascading vasomodulating signal using overlapping consecutive pairs of electrodes. For example, in a catheter having three electrodes, the signal generator can send a signal using the first and second electrodes and then another signal by using the second and third electrodes. In this manner, vasomodulation may be performed along a greater length of the guide catheter than would be possible with using only two electrodes.

In one method of use, a guide catheter of this embodiment may be used to treat vasospasms as described above with respect to the tip electrode guide catheter embodiments. Some vasospasms may not occur or may not be detected until after the tip of the guide catheter is past the area of vasospasm. Vasomodulation may be applied by using the two electrodes nearest the area of vasospasm or, alternatively, along the length of the electrodes as described above.

In another method of use, the guide catheter may be used to apply vasorestriction in conjunction with another therapy. For example, a guide catheter is advanced to a desired location in a blood vessel and an angioplasty catheter is advanced within the guide catheter. Vasorestriction is applied around the guide catheter proximal of the distal end. The blood vessel constricts around the guide catheter to reduce or stop blood flow. This may be done just prior to advancing the angioplasty catheter across the occlusion to prevent fragments from drifting downstream or to localize the application of a therapeutic agent by stopping the flow of blood. When blood flow is desired again, perhaps to reperfuse or flush the area of treatment, the vasoconstriction can be reversed by applying a vasodilating signal with the electrodes. This is a quick procedure and may be repeated throughout the overall treatment as desired. In this manner, the vasomodulating catheter may be used as an alternative to a guide catheter having a balloon or other mechanical occluder at its distal tip. Alternatively such a procedure can be used to avoid the associated side effects of a larger dispersal of drugs by localizing the treatment area.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
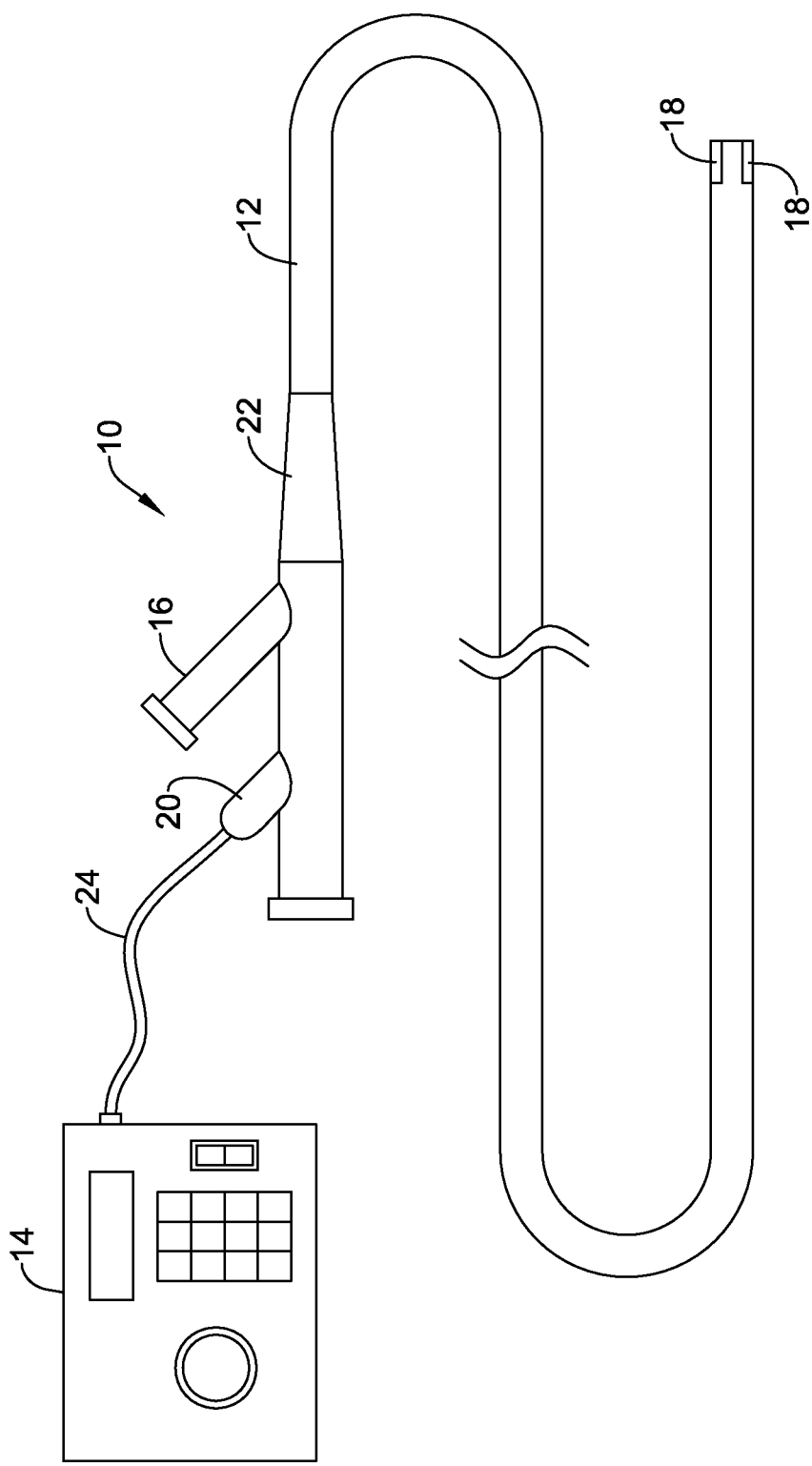
FIG. 1 is a diagrammatic view of a guide catheter system according to one embodiment of the invention.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Further, the description of the embodiments is made generally with reference to use within the vasculature and with guide catheters. However the invention is not so limited. Embodiments of the invention and methods of use thereof may become an integral part of any catheter used in a catheter-based procedure that involves lumens lined with smooth muscle, which procedures may include vascular, cardiology, pulmonary, gastrointestinal, urology, gynecology and peripheral vascular procedures, among others.

As used herein, a circuit means a configuration of electrically or electromagnetically connected components or devices or a subset thereof. The term circuit may, in certain contexts, refer to any of electrical, electronic, or software components.

As used herein, an electrode means a solid electric conductor through which an electric current enters or leaves an electrolytic cell or other medium, and which is distinct from other electrodes. One electrode may not be connected to another or may be electrically connected to another through the impulse generating system or other distinct part of the circuit or may be connected directly only electromagnetically. Two sections of the same electric conductor are a single electrode.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Turning now to FIG. 1, a guide catheter system 10 includes a guide catheter 12 and an electrical impulse generator 14. Guide catheter 12, apart from the additional features discussed herein, may include any features of a guide catheter not expressly discussed, including, for example, a hub 16 having one or more ports, one or more lumens, layered or reinforced construction, radiopaque features and sensors. Guide catheter 12 may also include one or more electrodes 18 disposed at the distal tip of the catheter.

Electrodes 18 may be made from any electrically conductive materials, including metals, electrically conductive polymers or ceramics, electrically conductive paints or coatings or any other suitable material. The electrode may be attached to the catheter through any conventional means suitable to the material, including molding the electrode in place, adhesives, welding, a tie layer or other means. The electrodes are depicted as solid but may have a flexible geometry such as an open mesh. Each electrode is electrically connected to a connector 20 by a wire or other conduit (not shown). These wires may be embedded within the wall of the catheter 12, disposed on the inside wall of the catheter, painted on using an electrically conductive paint or fashioned using some other suitable method. Electrodes 18 are on the outside surface of the catheter and preferably exposed to elements distal of the distal tip of the catheter. Electrodes 18 are preferably visible using radioscopic techniques or, alternatively, a radiopaque element is disposed near the electrodes.

Hub 16 includes one or more ports and a strain relief 22 and may include a connector 20. Connector 20 permits the catheter to be easily and releasably connected via a cord or wires 24 to electrical impulse generator 14. Any suitable means of connecting the catheter electrodes electrically to the electrical impulse generator may be used. In an alternative embodiment, each electrode may be separately connected to the electrical impulse generator, and consequently, only the electrodes being used need to be connected.

Electrical impulse generator 14 includes a power source such as a battery or power cord for connecting to external power, a circuit for controlling the waveform characteristics of the electrical impulse, and means for sending the electrical impulse through the electrodes and suitable controls. The circuit for controlling the waveform characteristics may include means for customizing the frequency, voltage, length of pulses and number of pulses, or overall duration or means for selecting preloaded waveform characteristic profiles. One example electrical impulse waveform known to cause vasodilation is a pulse of about 1 hertz and up to 70 volts. One example electrical impulse waveform known to cause vasoconstriction is between about 10 and about 20 volts and greater than about 16 hertz. Other therapeutically effective waveforms may be used as well. The waveform profile may be selected as well. For example, a sinusoidal pulse or a square wave pulse may be selected as desired.

Figure 2A:
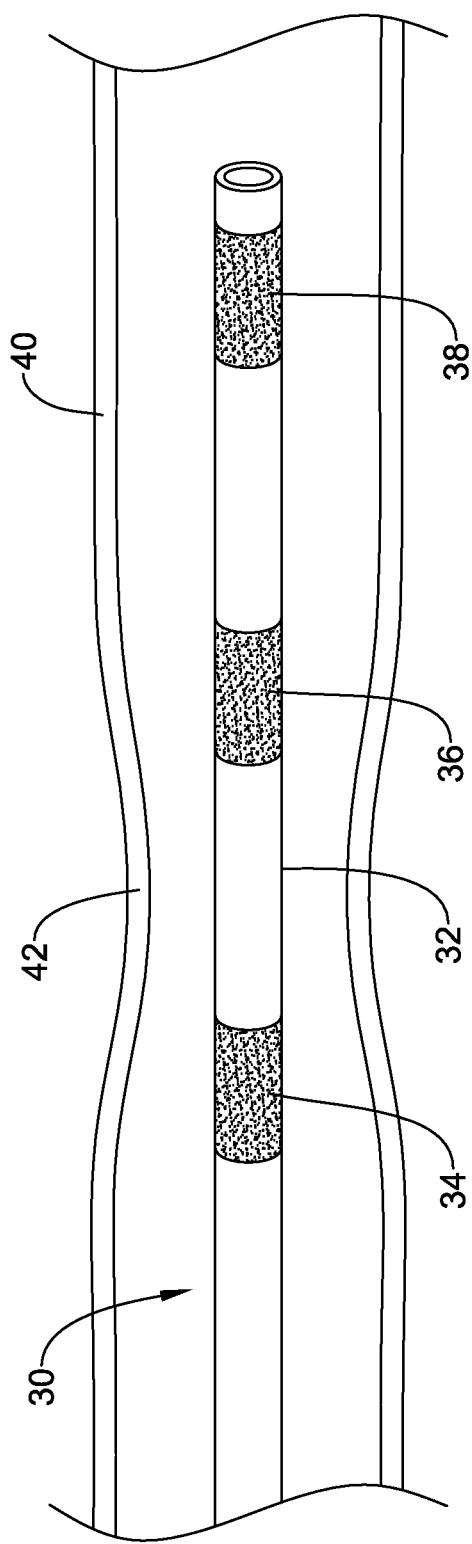
FIG. 2A is a diagrammatic view of the distal end of a second embodiment of a guide catheter system disposed in a blood vessel.

FIG. 2A depicts the distal part of a guide catheter system 30. Guide catheter system 30 is similar to guide catheter system 10 except as discussed herein. System 30 includes a guide catheter 32 with electrodes 34, 36, and 38 spaced apart longitudinally along the outer surface of the guide catheter near the distal end. More or fewer electrodes may be included as desired. The distance between each pair of electrodes is such that each pair (in this case, electrodes 34 and 36 or electrodes 36 and 38) may serve as the anode and the cathode of a bipolar electrode system. The electrodes are shown as having a cylindrical shape extending around the circumference of the guide catheter. Other shapes may be suitable, including a coil, a wire mesh or an electrode that does not fully encircle the guide catheter.

An electrical impulse generator (not shown) permits the functions described above with respect to electrical impulse generator 14 and also permits selection of which electrodes are used to deliver an electrical pulse. Any consecutive pair of electrodes (in this case, electrodes 34 and 36 or electrodes 36 and 38) may be selected. Another function of the electrical impulse generator may be to deliver pulses through more than one pair of electrodes to vasomodulate along a greater length of the catheter. For example, a profile may be loaded into the electrical impulse generator that sends a rapid succession of pulses cascading through alternating pairs of electrodes or sequentially down the line of electrode pairs.

Figure 2B:
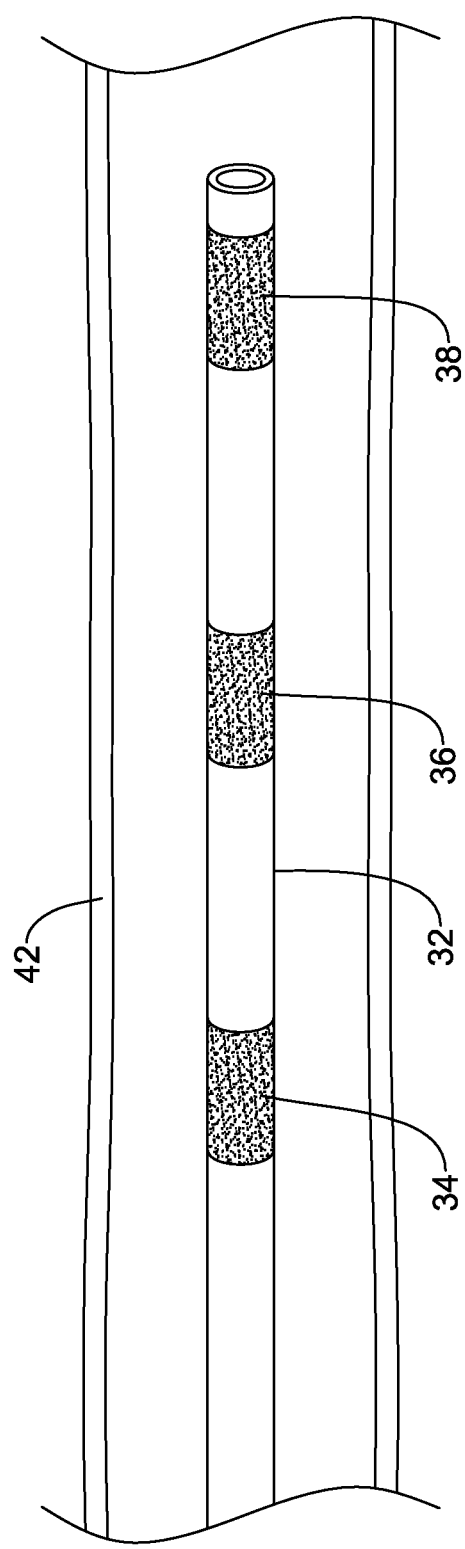
FIG. 2B is a diagrammatic view of the distal end of the system of FIG. 2A disposed in the blood vessel.

In FIG. 2A, the distal part of the guide catheter 32 is depicted as disposed in a blood vessel 40 having a constriction 42 caused by a vasospasm. The location of the vasospasm relative to the guide catheter may be determined fluoroscopically and electrode pair 34 and 36 may be selected using the electrical impulse generator. A vasodilating electrical impulse is sent through the selected electrodes to treat the vasospasm by dilating the blood vessel wall near the selected electrodes as shown in FIG. 2B. The blood vessel may be dilated to its nominal diameter, as depicted, or may be dilated to an enlarged profile if desired.

The above describes only the procedures unique to the particular guide catheters of this and other embodiments. Other elements of a procedure, such as advancing the guide catheter over a guidewire, advancing a therapeutic catheter such as an angioplasty or stent delivery catheter, or the application of therapeutic agents may, of course, be performed as with any guide catheter. In fact, the electrical impulse generator may not need to be connected and the guide catheter may be used as if it were a standard guide catheter. Only if a vasospasm or other condition amenable to treatment with vasomodulation is detected need the above procedure be employed.

Figure 3:
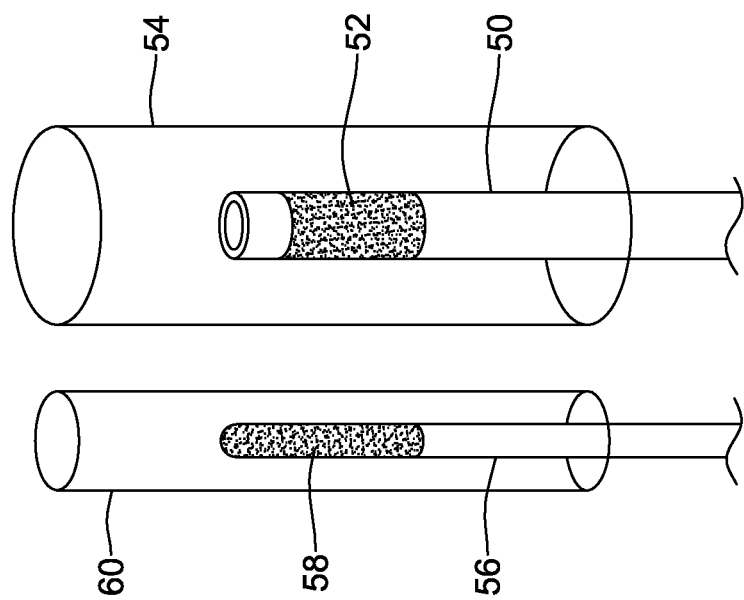
FIG. 3 is a diagrammatic view of the distal ends of another embodiment of a guide catheter system disposed in a blood vessel.

FIG. 3 is a diagrammatic view of the distal ends of an embodiment of the invention. Depicted is the distal end of a guide catheter 50 having an electrode 52 disposed thereon in a first blood vessel 54 and the distal end of an elongate instrument 56 having an electrode 58 disposed thereon disposed in a second blood vessel 60. The first and second blood vessels may be any two blood vessels that run close together. For example, the aorta and the vena cava are suitable blood vessels. Electrodes 52 and 58 may be any suitable electrode as described above and elongate instrument 56 may be a guidewire or other suitable device. The guide catheter may include more than one electrode to allow flexibility in choosing the treatment location without moving the guide catheter.

In use, guide catheter 50 is used as desired in a therapeutic process such as an angioplasty procedure. Should a vasospasm or other condition amenable to treatment with vasomodulation be detected, elongate instrument 56 is advanced through second blood vessel so that the electrode is near the vasospasm. Both the guide catheter and the elongate instrument are electrically connected to an electrical impulse generator, and a vasomodulation therapy is performed to treat the vasospasm. If the guide catheter includes more than one electrode, the electrode near the area of treatment is selected using the electrical impulse generator prior to performing the vasomodulation.

Those skilled in the art will recognize that the present invention may be manifested in a variety of forms other than the specific embodiments described and contemplated herein. For example, it will be readily apparent that electrodes 18 may be combined into guide catheter system 30. Accordingly, departure in form and detail may be made without departing from the scope and spirit of the present invention as described in the appended claims.

What is claimed is:

1. A method of advancing a guide catheter, comprising the steps of:
 providing a guide catheter having a proximal hub, a distal tip and a lumen extending therebetween, the guide catheter further having an electrode disposed at the distal tip;
 determining a location of a vasospasm in a blood vessel where the vessel is constricted;
 advancing the distal tip of the guide catheter distally to a first location within the blood vessel, wherein the first location is proximal of the vasospasm;
 applying an electrical impulse through the electrode to the blood vessel to cause the blood vessel to dilate at the first location;
 advancing a balloon catheter distally through the guide catheter to a location distal of the first location; and
 expanding the balloon distal of the distal tip of the guide catheter.

2. The method of claim 1, further comprising, subsequent to the step of applying the electrical impulse, the step of advancing the guide catheter to a second location distal of the first location.

3. The method of claim 2, further comprising the step of applying an electrical impulse through the electrode to the blood vessel to cause the blood vessel to dilate at the second location.

4. The method of claim 1, wherein the guide catheter further comprises a second electrode at the distal tip of the catheter and wherein the step of applying the electrical impulse further includes the step of applying the electrical impulse through the second electrode.

5. The method of claim 1, further comprising the step of observing the blood vessel.

6. The method of claim 5, wherein the step of observing the blood vessel includes the step of observing the blood vessel fluoroscopically.

7. The method of claim 1, wherein the guide catheter further includes a third electrode spaced proximally from the distal tip and further including the steps of moving the guide catheter so that the third electrode is near the observed vasospasm and applying an electrical impulse through the third electrode to the blood vessel to cause the blood vessel to dilate at the location of the observed vasospasm.

8. The method of claim 1, wherein the guide catheter is slowly advanced distally while applying the electrical impulse.

9. The method of claim 1, wherein the electrode is in contact with a wall of the blood vessel during the step of applying an electrical impulse.

10. A method of performing an intravascular therapeutic procedure comprising the steps of:
 providing a guide catheter having a distal end and a lumen and an electrode disposed near the distal end;
 providing a therapeutic instrument configured to be inserted through the guide catheter;
 advancing the distal end of the guide catheter through a blood vessel to a location proximal of a region to be treated;
 applying an electrical impulse through the electrode to constrict the blood vessel around the guide catheter;
 while the blood vessel is constricted, advancing the therapeutic instrument through the guide catheter and out of the distal end of the guide catheter to the region to be treated;
 performing a therapeutic procedure with the therapeutic instrument; and
 applying an electrical impulse through the electrode to dilate the blood vessel.

11. The method of claim 10, wherein the step of applying an electrical impulse to constrict the blood vessel and the step of applying an electrical impulse to dilate the blood vessel are alternated and repeated throughout the therapeutic procedure.

12. The method of claim 10, wherein the step of applying an electrical impulse to constrict prevents blood flow past the guide catheter electrode.

13. The method of claim 10, wherein the guide catheter includes a second electrode.

14. A guide catheter system comprising:
 a guide catheter having a proximal end and a distal end and a first plurality of electrodes disposed at the distal end, the first plurality of electrodes electrically connected to an electrical impulse generator; and
 a second plurality of electrodes disposed on a guide wire, the second plurality of electrodes electrically connected to the same electrical impulse generator as the first plurality of electrodes, wherein the guide wire is disposed outside of the guide catheter such that the guide catheter and guide wire are configured to be inserted into different vessels while remaining connected to the electrical impulse generator.

* * * * *